US006626567B2

(12) United States Patent
Boiarski

(10) Patent No.: US 6,626,567 B2
(45) Date of Patent: Sep. 30, 2003

(54) COOLING SYSTEM FOR THERMAL ANALYSIS

(76) Inventor: Mikhail Boiarski, 5373 Princeton Rd., Macungie, PA (US) 18062

( * ) Notice: Subject to any disclaimer, the term of this patent is extended or adjusted under 35 U.S.C. 154(b) by 0 days.

(21) Appl. No.: 09/904,171

(22) Filed: Jul. 12, 2001

(65) Prior Publication Data

US 2002/0018509 A1 Feb. 14, 2002

Related U.S. Application Data

(60) Provisional application No. 60/217,957, filed on Jul. 13, 2000.

(51) Int. Cl.[7] .......................... G01N 25/00; G01K 17/00
(52) U.S. Cl. ........................ 374/11; 374/10; 374/31
(58) Field of Search ................... 374/10, 11, 12, 374/31; 62/51.1

(56) References Cited

U.S. PATENT DOCUMENTS

| | | | | |
|---|---|---|---|---|
| 4,140,989 A | * | 2/1979 | Baixeras et al. ............... 338/25 |
| 5,098,196 A | * | 3/1992 | O'Neill ........................ 374/11 |
| 5,211,477 A | * | 5/1993 | Li ................................ 374/10 |
| 5,337,572 A | * | 8/1994 | Longsworth ................ 62/51.2 |
| 5,579,654 A | * | 12/1996 | Longsworth et al. ......... 62/51.3 |
| 5,595,065 A | * | 1/1997 | Boiarski et al. .............. 62/51.2 |
| 5,687,574 A | * | 11/1997 | Longsworth et al. ......... 62/55.5 |
| 5,724,832 A | * | 3/1998 | Little et al. .................... 62/613 |
| 5,876,118 A | * | 3/1999 | Vogel ........................... 374/11 |

\* cited by examiner

*Primary Examiner*—Diego Gutierrez
*Assistant Examiner*—Mirellys Jagan
(74) *Attorney, Agent, or Firm*—Katten Muchin Zavis Rosenman

(57) ABSTRACT

A cooling system for thermal analysis equipment provides rapid cool down and steady state operation of a differential scanning calorimeter (DSC) at any predetermined temperature between a minimal temperature and room temperature using a throttle-cycle cooler based on a single stage compressor. The cooling system operates with a mixed refrigerant that includes some liquid fraction at the inlet to a cryostat that houses the key cold elements for the cooling system. A temperature actuated automatic throttle valve in the cooling system increases refrigerant mass flow rate when the differential scanning calorimeter increases the heat load (and vice-versa) that is generally provided by a heater. At the same time, the valve design provides a high mass flow during cool down and automatic flow rate reduction at an intermediate temperature as the overall system approaches an operating condition during cool down.

11 Claims, 5 Drawing Sheets

COOLING SYSTEM FOR THERMAL ANALYSIS

This application claims the benefit of earlier filed and pending provisional application No. 60/217,957.

BACKGROUND OF THE INVENTION

The present application relates to a throttle-cycle cooler operating with mixed refrigerant (MR) that provides functionality of instruments in the field of thermal analysis. Specifically, a differential scanning calorimeter (DSC) is a basic instrument used in thermal analysis.

Thermal analysis is widely used in various applications including the pharmaceutical and food industries, material science, electronics, etc. The analysis is based on a comparison of the calorimetric properties of a sample to be investigated, analysis sample (AS), and a reference sample (RS) with calibrated properties.

The samples are placed in containers located on a plate, with plate temperature regulated in a range of $T_{MAX}$ to $T_{MIN}$. Any temperature in this range is supported precisely by the temperature control system, which regulates power of a heater attached to a hot plate as shown in FIG. 1. A cooling system incorporated in the DSC provides a cold plate temperature. The cold plate is connected to the hot plate with a thermal bridge that is a thermal resistor. The balance between input heater power and cooling capacity of the cooling system provides accuracy of measurements and rapid transition time from one temperature point to another in a typical temperature range of $T_{MAX}$=700 C. (973K.) to $T_{MIN}$=−150 C. (123K.), and −195 C. (78K.) in some application. Existing cooling systems provide $T_{MIN}$ that depends on the field of application of the thermal analysis, such as:

$T_{MIN}$=−170 C. for glass transaction, polymorphism, purity, dynamic mechanical analysis;

$T_{MIN}$=−150 C. for thermo-mechanical analysis, expansion coefficient, penetration;

$T_{MIN}$=−50 C. (223K.) for laser flash methods: thermal diffusivity of ceramics, alloys, fibers;

$T_{MIN}$>−50 C. for thermal gravimetry.

A cooling system (CS) in a current design might be one of different types depending on the temperature range that is selected for analysis. For example, air cooling is useful through a range +50 C. (323K.) to +100 C. (373K.). Closed-cycle coolers that use conventional refrigerants may be used when providing temperatures down to −50 C., and a system based on liquid nitrogen can provide cold plate temperatures down to −195° C.

A major disadvantage of existing cooling systems employed in a DSC below −50 C. is that they depend on a liquid nitrogen supply and boil-off system. Such a system increases the operating cost of the DSC. The electronic temperature control system is complicated because of a high temperature difference between the hot plate and cold plate. In addition, refilling required for liquid nitrogen use does not allow continuous long-term operation for automatic analysis of samples.

An object of this invention is to provide a closed-cycle cooler to support functionality of the thermal analysis instruments and specifically a DSC at minimal temperature below room temperature down to −183 C. (90K.)

Another object of this invention is to develop a cooler that easily allows a customized interface with thermal analysis instruments including DSCs of different configurations to operate in a predetermined temperature range.

SUMMARY OF THE INVENTION

Generally speaking, in accordance with the invention, a cooling system for thermal analysis equipment and the like provides rapid cool down and steady state operation of a differential scanning calorimeter (DSC) at any predetermined temperature between a minimal temperature and room temperature using a throttle-cycle cooler based on a single stage compressor. In the cooling system, the cooler operates with a mixed refrigerant that may include some liquid fraction at the inlet to a cryostat that houses the key cold elements for the cooling system. A temperature actuated throttle valve in the cooling system increases refrigerant mass flow rate when the differential scanning calorimeter increases the heat load, generally provided by a heater. At the same time, the valve design provides a high mass flow during cool down, and automatic flow rate reduction at an intermediate temperature as the overall system approaches an operating condition after cool down.

Still other objects and advantages of the invention will be apparent in the specification.

The invention accordingly comprises the features of construction, combination of elements, and arrangement of parts, which will exemplified in the constructions hereinafter set forth, and the scope of the invention will be indicated in the claims.

BRIEF DESCRIPTION OF THE DRAWINGS

For a fuller understanding of the invention, reference is made to the following description taken in connection with the accompanying drawings, in which.

DESCRIPTION OF THE PREFERRED EMBODIMENTS

Figure 1:
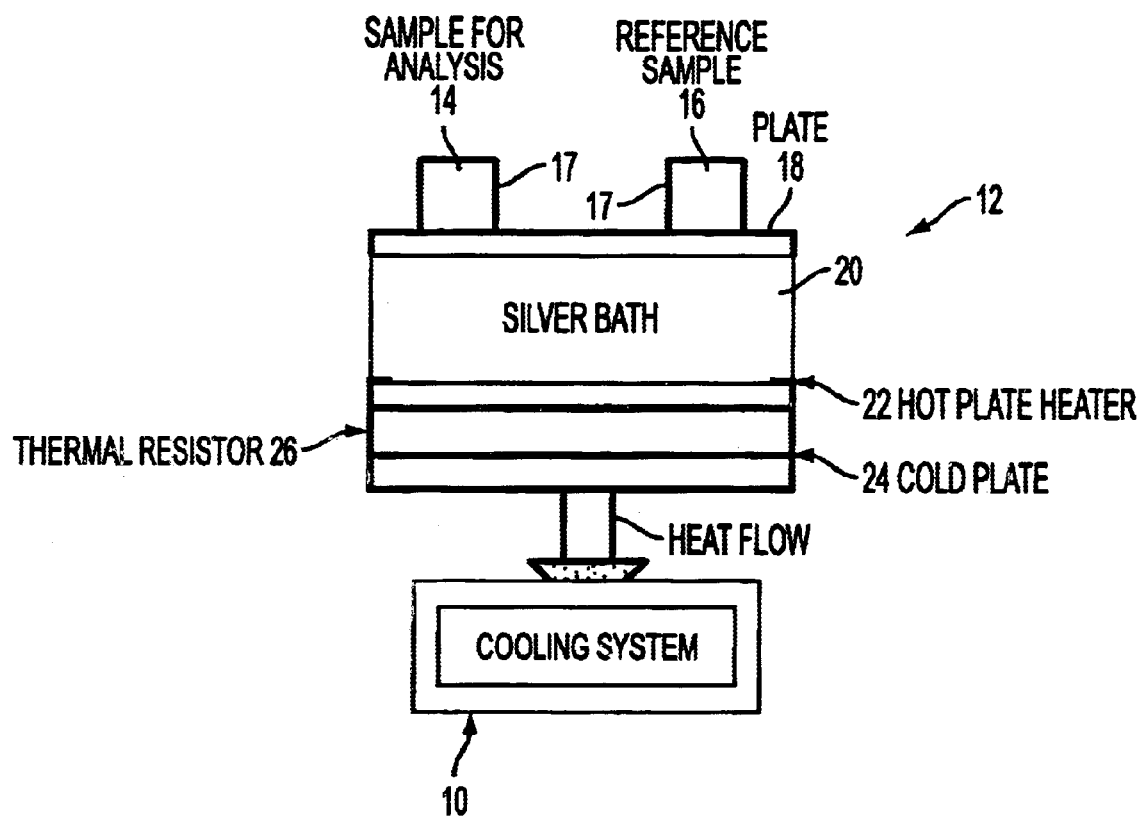
FIG. 1 is a schematic diagram of a differential scanning calorimeter.

With reference to FIG. 1, a cooling system 10 in accordance with the invention is connected to a differential scanning calorimeter 12 that is conventional in the art. In thermal analysis using a differential scanning calorimeter, a sample 14 for analysis and a reference sample 16 in containers 17 rest on a plate 18. The reference sample 16 has calibrated thermal properties. The temperature of the plate 18 can be regulated by the cooling system 10 in a temperature range of $T_{MAX}$ to $T_{MIN}$. As illustrated, the plate 18 rests on a silver bath 20. Generically, the element 20 is a high thermal conductivity material in thermal contact with the plate 18. The bath 20 rests on a hot plate/heater 22, that is, a plate with an electrical heater attached thereto to heat the bath 20.

A temperature control system (not shown) precisely regulates the power supplied to the heater attached to the hot plate. A cold plate 24 is separated from the hot plate/heater 22 by a thermal resistor 26 that is a material having a high thermal conductivity when it is cold and a low thermal conductivity when it is hot, for example, a sapphire material.

The cooling system 10 provides cooling for the cold plate 24 as described in greater detail hereinafter with reference to FIG. 2.

The cooling system 10 includes (FIG. 2) a compressor 28 having its high-pressure gas discharge connected to an aftercooler 30 where the refrigerant is cooled and thermal energy is rejected from the cooling system 10. Refrigerant flowing from the aftercooler 30 enters the heat exchanger 32 and from there passes through a throttle device 34 that reduces refrigerant pressure. From the throttle device, the refrigerant flows through an evaporator 36 where the refrigerant is in heat exchange relationship with and cools the cold plate 24 of the differential scanning calorimeter.

From the evaporator 36, the refrigerant, having absorbed thermal energy from the plate 24, flows to the heat exchanger 32 where it is in a heat exchange relationship, here illustrated as counterflow, with the refrigerant flowing from the aftercooler 30 to the throttle device 34. Leaving the heat exchanger 32, the refrigerant having absorbed more thermal energy, returns to the low-pressure inlet to the compressor 28, and the refrigerating cycle is repeated in the known manner.

Figure 2:
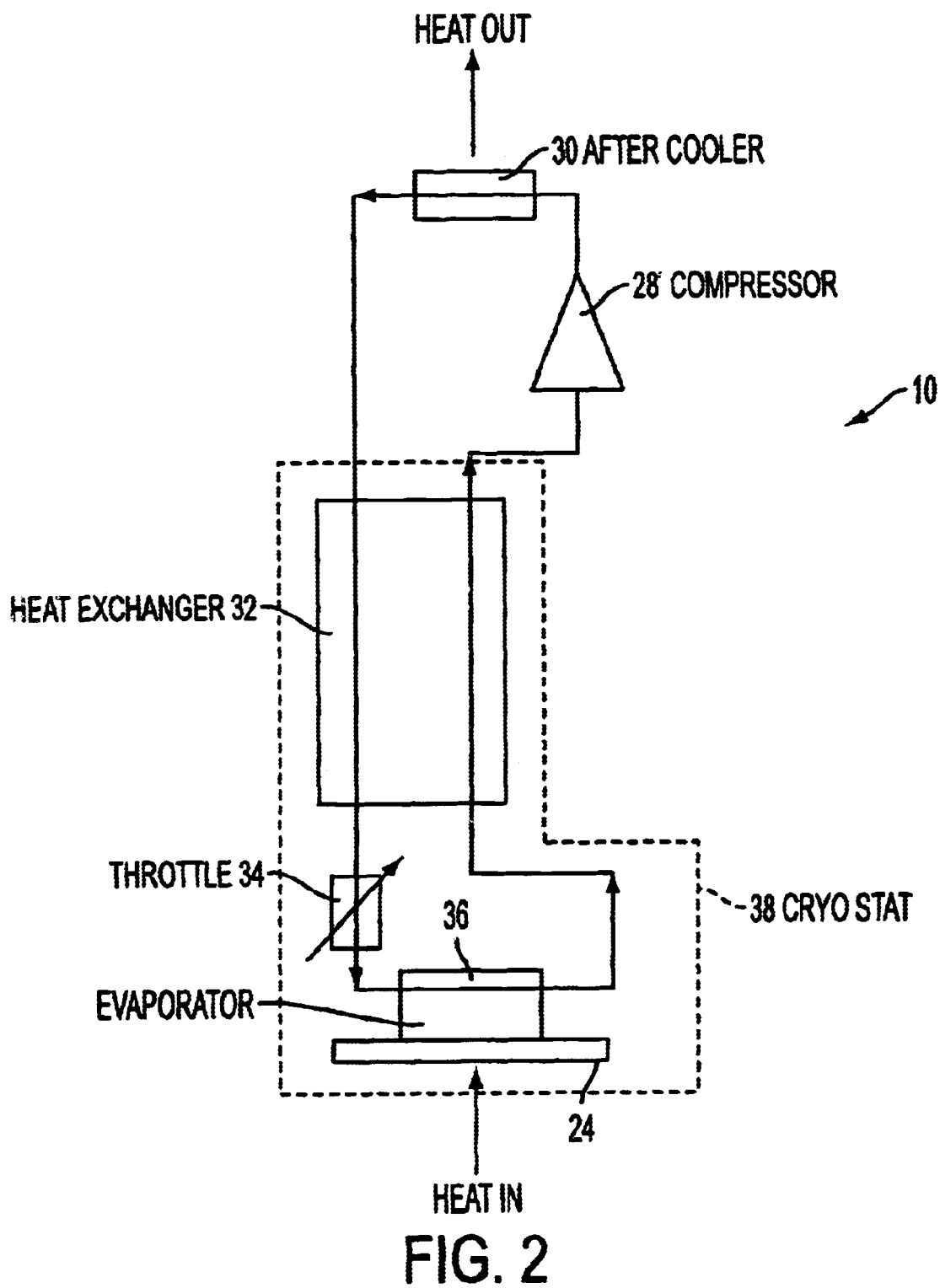
FIG. 2 is a schematic diagram of a throttle cycle cooler used in accordance with the invention.

The cold elements of the cooling system 10 are contained in an insulated cryostat 38 represented by the broken lines in FIG. 2. The cryostat 38 is insulated, for example, with vacuum insulation, foam, etc. The compressor 28 is of single stage construction operating with a mixed refrigerant that may provide some liquid fraction at the inlet to the cryostat 38 and throttle 34 after leaving the aftercooler 30 and heat exchanger 32.

The throttle device 34 is a temperature-actuated throttle valve that increases refrigerant mass flow rate when the differential scanning calorimeter heater in the hot plate/heater 22 increases the applied heat load (and vice-versa) in operation of the differential scanning calorimeter. The valve design also provides a high refrigerant mass flow during cool-down and automatic flow rate reduction at an intermediate temperature as the system approaches an operating temperature for measurements of the differential scanning calorimeter.

Such an automatic throttle device is disclosed in U.S. Pat. No. 5,595,065, which has a common owner with the present application and is incorporated herein by reference. U.S. Pat. No. 5,337,572 has a common owner with the present application and also is incorporated herein by reference. This patent defines a refrigeration system and mixed refrigerant which can operate with the above-mentioned automatic throttle device to practice the invention.

The construction of the cryostat 38 allows a simple interface with the differential scanning calorimeter cold plate 24 and the heat exchanger 32 is compact and may be located close to or remotely from the evaporator 36.

This cooling system 10, is based on a single stage compressor operating in a throttle-cycle cooler using a mixed refrigerant to provide functioning for thermal analysis equipment, specifically, a differential scanning calorimeter operating at temperatures below the ambient temperature down to 90°K. Such a closed cycle cooling system 10 replaces use of a liquid nitrogen evaporative cooler. Rapid cool down and steady state operation of the differential scanning calorimeter at any predetermined temperature between 90° K. and room temperature are accomplished with this cooling system 10.

In operation of a differential scanning calorimeter, the analysis sample 14 and the reference sample 16 are subjected to a range of different temperatures while measurements are made. Different temperatures are achieved by varying the amount of heat applied to the heater in the hot plate/heater 22. The cooling system 10 operates continuously as the temperature of the samples is varied. The valve 34 automatically adjusts to control the refrigerant flow rate and temperature at the cold plate 24.

The difficulties associated with the design of a cooler for a DSC are reduced by the present invention. These difficulties include a necessity to provide high refrigeration capacity at the lowest temperature $T_{MIN}$ that supports the heat flux from the hot plate/heater 22. It is necessary that the components of the cooling system 10 that attach to the DSC cold plate 24 be of small size. The cooling system 10 should not generate an excessive noise or mechanical vibration that can degrade operation of the differential scanning calorimeter. Cool down time provided by the cooling system 10 should quickly make the differential scanning calorimeter ready for measurements. The cooling system 10 should have low power consumption to reduce differential scanning calorimeter operational expenses. The cooling system 10 should operate reliably at any heat load less than its maximum capability $Q_{MAX}$ and provide long term reliability. The compressor unit 28 may be located far from the cryostat 38 to reduce noise and vibration and not obstruct an easy integration of the cooling system 10 and the differential scanning calorimeter at the cold plate 24.

As will be obvious to those skilled in the art, many of these requirements are in conflict with each other in designing a cooling system. None of the traditional type coolers like GM, vapor-compression cycle, or Stirling can satisfy all of the above-mentioned specifications.

Figure 3:
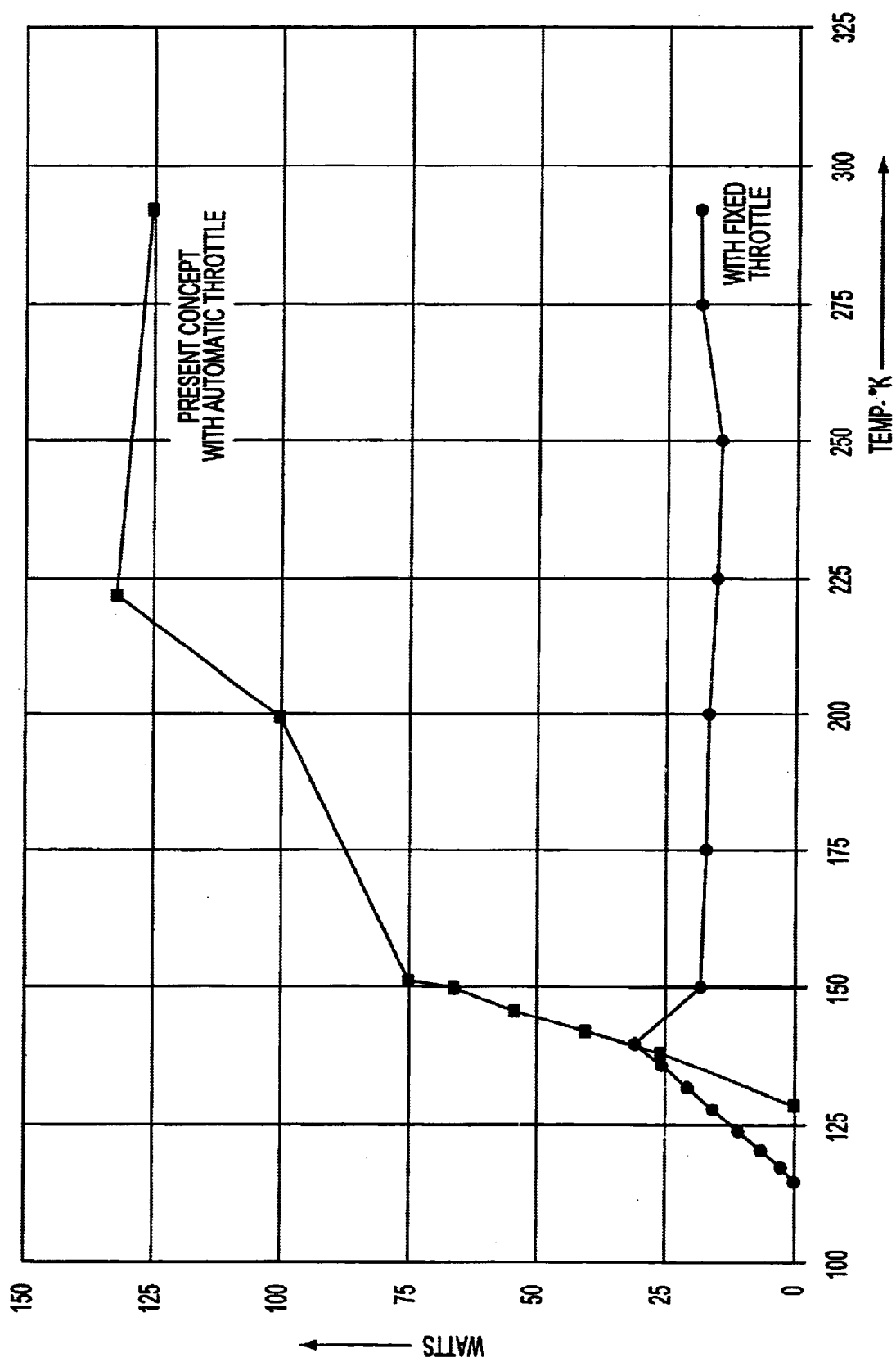
FIG. 3 is a chart comparing cooling system capacity in watts versus cold plate temperature (test values with heat applied after cooldown) for a fixed throttle and for the present invention with an adjustable throttle.

The cooling system 10 of FIG. 2 using the throttle-cycle cooler operating with mixed refrigerant that provides high refrigeration performance, is the closest approach to satisfying all of the requirements. A system with a fixed throttle, for example as shown in the lower curve of FIG. 3, tolerates a heat load increase only in a relatively narrow temperature range. At temperatures above $T_{MAX}$, it is difficult to provide steady state operating conditions with the fixed throttle system. Further, additional problems would be provided when operating in a broad temperature range from $T_{MIN}$ up to room temperature to provide scanning by changing the heater power.

In tests, the throttle cycle cooler 10 of FIG. 2, based on a single-stage oil-lubricated compressor (see U.S. Pat. No. 5,579,654, which is also incorporated herein by reference) satisfied performance requirements for a differential scanning calorimeter when operating with mixed refrigerants. The mixed refrigerant composition was selected to provide a partially liquefied refrigerant flow at the high pressure inlet to the counterflow heat exchanger 32 after leaving the aftercooler (condenser) 30. In addition, the temperature-actuated throttle valve, particularly one using a bimetal, provided suitable cool down and operating characteristics. Experimental results are illustrated by the upper curve in FIG. 3 for the present invention. The present invention using the temperature actuated throttle device, as described above, provides greatly increased cooling capacity as the load temperature increases.

Figure 4:
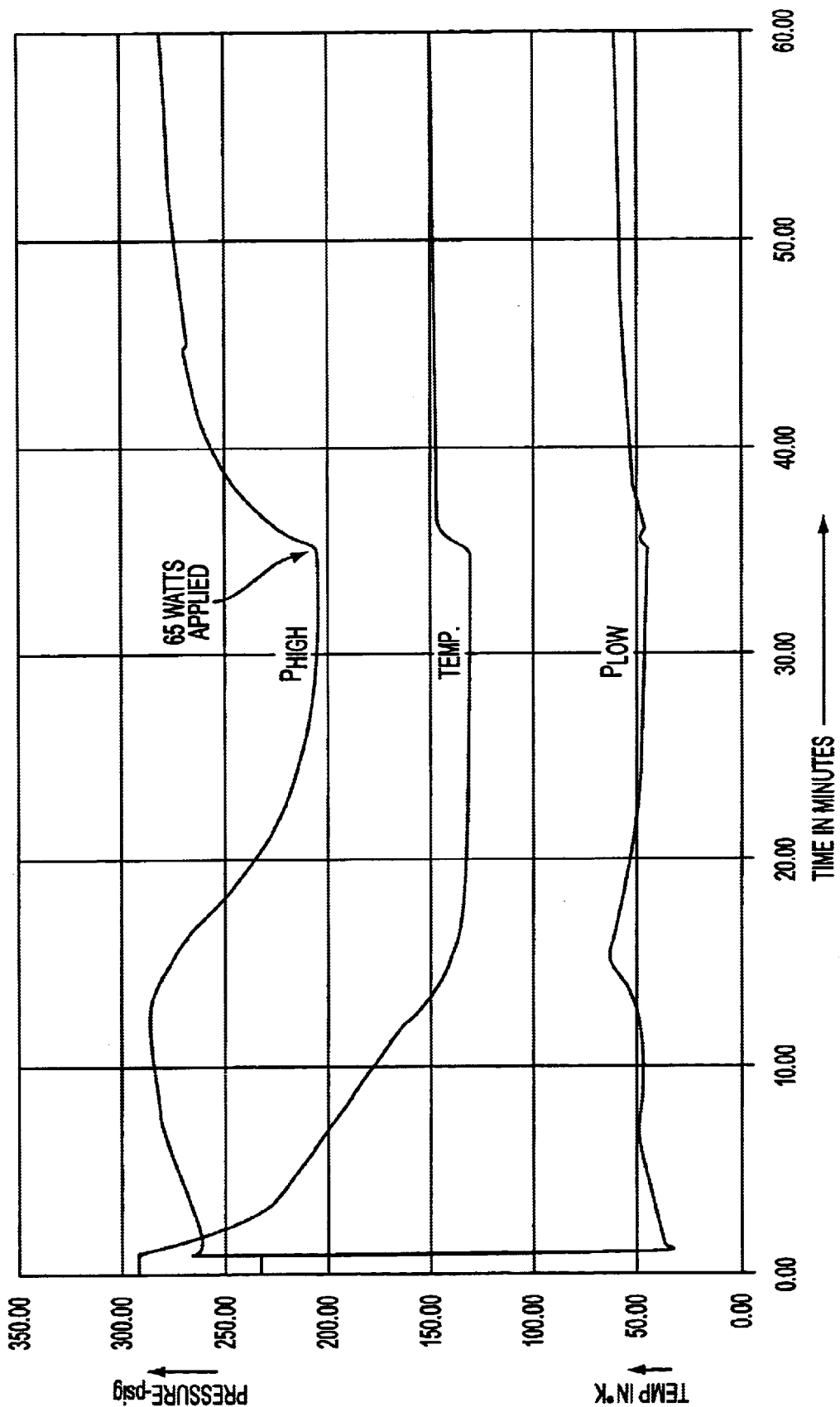
FIG. 4 is a graph of test pressures, high and low, and temperature characteristics for the cooling system in accordance with the invention using a throttle valve of U.S. Pat. No. 5,595,065 during cool down.

FIG. 4 shows characteristics of the present invention with temperature actuated throttle device during cool down when the differential scanning calorimeter is inoperative. There are two separate scales on the ordinate, namely, pressure and temperature. The abscissa represents elapsed time. The compressor discharge pressure, P high, and compressor inlet or return pressure, P low, are illustrated. Of importance, is the temperature curve indicating the temperatures provided at the cold plate 24 of a differential scanning calorimeter. In the graph, the temperature drops from approximately 290K to approximately 135K in less than twenty minutes. The temperature response is rapid when 65 watts of energy are later applied to the hot plate/heater 22.

Figure 5:
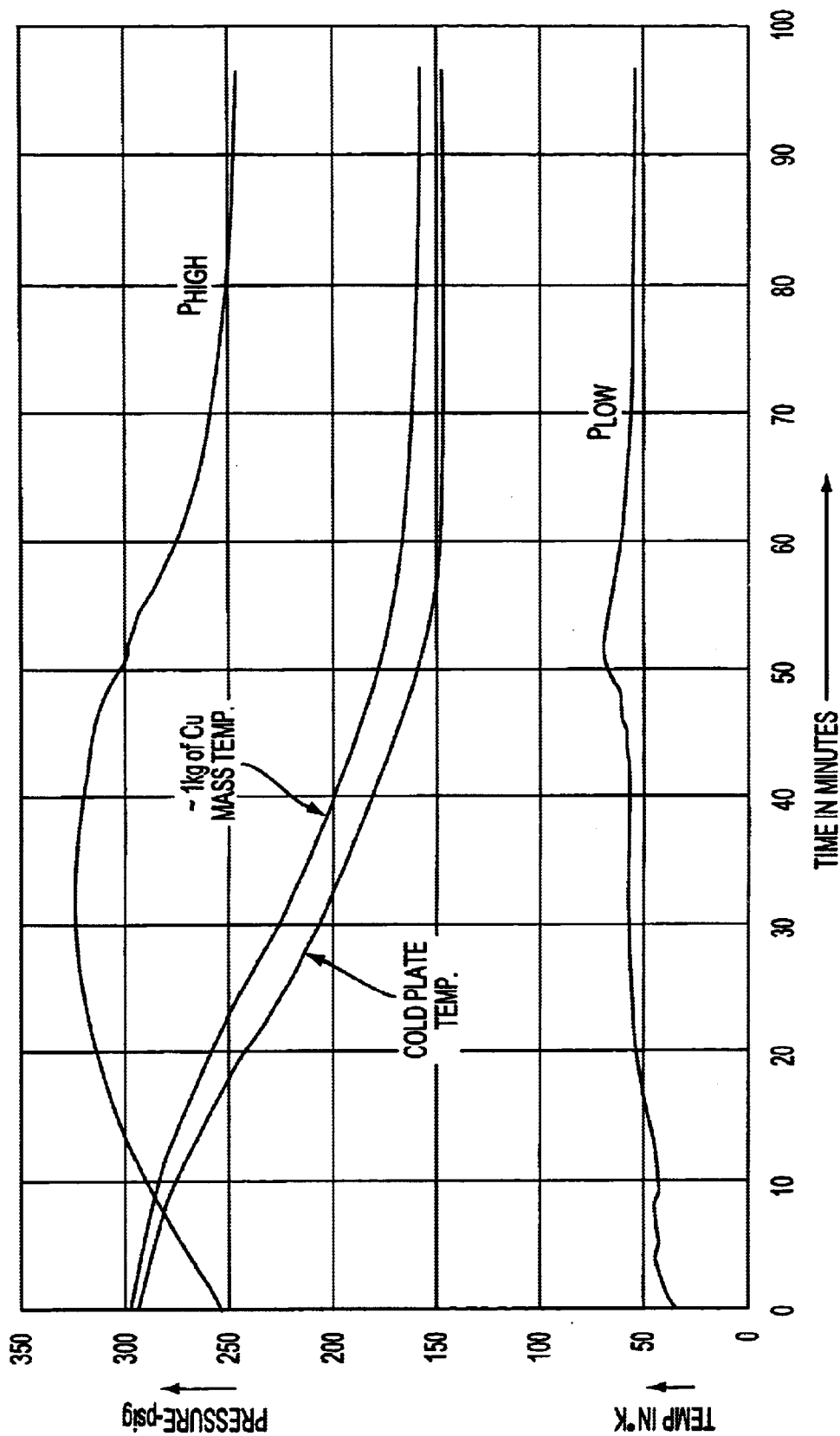
FIG. 5 indicates test characteristics of the cooling system during cool down when attached to a differential scanning calorimeter.

FIG. 5 is similar to FIG. 4 except that it shows operation of the cooling system when the differential scanning calorimeter is in operation with samples 14, 16 in place on the plate 18.

It will thus be seen that the objects set forth above, among those made apparent from the preceding description, are efficiently attained and, since certain changes may be made in construction without departing from the spirit and scope of the invention, it is intended that all matter contained in the above description and shown in the accompanying drawings shall be interpreted as illustrative and not in a limiting sense.

What is claimed is:

1. An apparatus for thermal analysis comprising: a holder unit having a controlled temperature; a temperature control system for controlling said holder unit temperature, said control system including: a heater unit for adjustably providing heat to said holder unit; a cooling system for absorbing heat from said holder unit and said heater unit, a balance between said adjustable heater unit and said cooling system determining said controlled holder unit temperature, said cooling system having a single stage compressor operating with a mixed refrigerant in a closed cycle, wherein said apparatus is a differential scanning calorimeter, said heater unit is in heat transfer relationship with said holder unit by way of an intermediate material that contacts both said heater unit and said holder unit and is of high thermal conductivity material, said cooling system is in heat transfer relationship with said heater unit by way of an intervening thermal resistor that contacts both said heater unit and a cold plate that is cooled by said cooling system, said heater unit being located between said cold plate and said holder unit.

2. An apparatus for thermal analysis as in claim 1, wherein said highly conductive material is a silver bath.

3. An apparatus for thermal analysis as in claim 1, wherein said apparatus is a differential scanning calorimeter and in operation at least one sample is supported by said holder unit.

4. An apparatus as in claim 1 wherein a mixture of gas and liquid refrigerant enters said cryostat assembly.

5. An apparatus as in claim 1, wherein said cold plate is located remotely from a heat exchanger that is downstream of said refrigeration compressor and upstream of a throttle valve in said cooling system.

6. An apparatus for thermal analysis as in claim 1 wherein said cooling system uses an automatic throttle valve, said valve being in a cryostat and responding to increase refrigerant flow as the temperature of said holder unit increases and to decrease refrigerant flow as the temperature of said holder unit decreases.

7. An apparatus for thermal analysis as in claim 6, wherein a mixture of gas and liquid refrigerant enters said cryostat.

8. An apparatus for thermal analysis as in claim 6, wherein said throttle valve actuates automatically in response to the temperature of said holder unit.

9. An apparatus for thermal analysis as in claim 1, wherein said thermal resistor is a material having a high thermal conductivity when cold and a low thermal conductivity when hot.

10. An apparatus for thermal analysis as in claim 9 wherein said thermal resistor material is sapphire.

11. An apparatus for thermal analysis as in claim 10, wherein said thermal resistor cooling system runs continuously without adjustment during steady state operation and said temperature of said holder unit is varied by adjusting the input to said heater.

* * * * *